US006562984B2

(12) United States Patent
Peters et al.

(10) Patent No.: US 6,562,984 B2
(45) Date of Patent: May 13, 2003

(54) LACTONIZATION PROCESS

(75) Inventors: Theodorus H. A. Peters, Arnhem (NL); Frantisek Picha, Brno (CZ); Jacobus M. Lemmens, Mook (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 10/094,132

(22) Filed: Mar. 11, 2002

(65) Prior Publication Data

US 2002/0147351 A1 Oct. 10, 2002

(30) Foreign Application Priority Data

Mar. 9, 2001 (NL) ............................................. 1017548

(51) Int. Cl.⁷ ............................................. C07D 309/10
(52) U.S. Cl. ....................................................... 549/292
(58) Field of Search ......................................... 549/292

(56) References Cited

U.S. PATENT DOCUMENTS

| 4,444,784 A | 4/1984 | Hoffman et al. |
| 4,582,915 A | 4/1986 | Sleteinger et al. |
| 4,820,850 A | 4/1989 | Verhoeven et al. |
| 4,855,481 A | 8/1989 | Guindon et al. |
| 4,916,239 A | 4/1990 | Treiber |
| 5,159,104 A | 10/1992 | Dabora et al. |
| 5,223,415 A | 6/1993 | Conder et al. |
| 5,393,893 A | 2/1995 | Kubela et al. |
| 5,917,058 A | 6/1999 | Kumar et al. |
| 5,939,564 A | 8/1999 | Kumar et al. |

FOREIGN PATENT DOCUMENTS

| EP | 0 351 918 | 1/1990 |
| WO | 98/12188 | 3/1998 |
| WO | 98/32751 | 7/1998 |
| WO | 00/17150 | 3/2000 |

*Primary Examiner*—Taofiq Solola
(74) *Attorney, Agent, or Firm*—Fleshner & Kim, LLP

(57) ABSTRACT

Lactonization of statins can be achieved using a lactonization agent that forms a hydrated complex with the produced water that is insoluble in the reaction solvent. By binding the produced water in an insoluble complex, the reaction is pulled to the lactone side, using mild conditions in short reactions times and with reduced risk of impurities.

20 Claims, No Drawings

LACTONIZATION PROCESS

Antihypercholesterolemic compounds lovastatin and simvastatin are widely used in medicine for the lowering of levels of blood cholesterol. These compounds are derivatives of mevinic acid and have the following structural formula (1):

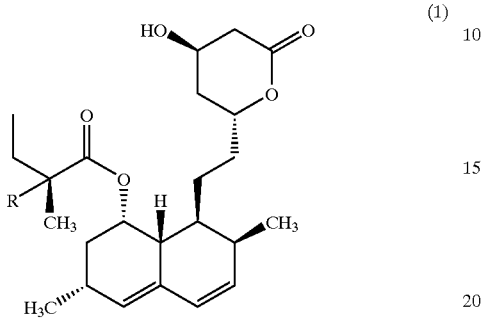

(1)

wherein when R=H, the compound is lovastatin and wherein when R=CH$_3$, the compound is simvastatin.

The chemical structure of both compounds includes the presence of a cyclic lactone moiety (4-hydroxy-3,4,5,6-tetrahydro-2H-pyran-2-one group) in the molecule. Accordingly, their chemical structure as expressed by the formula (1) may be simplified by the common formula (A),

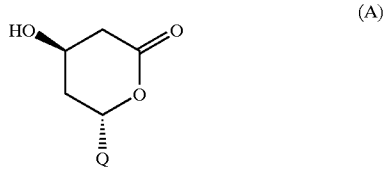

(A)

wherein Q represents the corresponding remaining part of the molecule of lovastatin or simvastatin.

Lovastatin is typically produced by a process that involves fermentation of various microorganisms while simvastatin is produced via a semi-synthetic or synthetic method as is known in the art. The fermentation methods for preparing lovastatin and/or simvastatin usually lead to the formation of a dihydroxyacid form (B) or a salt thereof

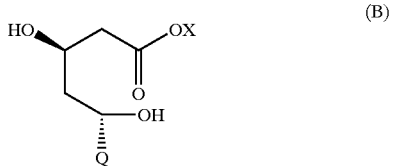

(B)

wherein X=hydrogen, metal cation, or ammonia cation, instead of or in addition to the desired lactone form (A).

Ammonium salts of the dihydroxyacid form are often used as intermediates in production methods as these salts are nicely crystalline. Acid and lactone forms may also be formed in the mixture. Whenever this occurs, it is necessary to convert the intermediate dihydroxyacid form (B) (or, accordingly, a salt thereof) into the desired lactone form (A).

Hereafter, the dihydroxyacid form (B) of compounds of formula (1) may be denoted as the "statin acid" or, if appropriate, "lovastatin acid" or "simvastatin acid" of formula (2).

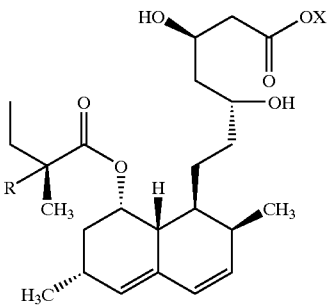

(2)

Wherein R and X are as hereinabove defined.

Lactonization is a process wherein a hydroxy acid loses one molecule of water to form an intramolecular ester—a lactone. This reaction is generally catalyzed by an acid; the necessary acidity arises either through the ambient acidity of the substrate itself or by an addition of a stronger acid, i.e. a lactonization agent, to enhance lactonization.

Lactonization is an equilibrium process characterized, in the case of statins, by the following equation:

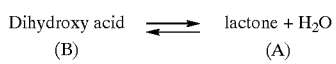

In order to obtain a high yield of the lactone product, some means is typically employed to shift the equilibrium to the lactone side of the equation. The common means of shifting the equilibrium to the lactone side (from (B) to (A)) is the removal of a reaction product from the reaction mixture.

One known way of removal of the reaction product during lactonization of a statin acid is the physical removal of produced water from the reaction mixture, e.g. by means of azeotropic distillation. In this arrangement, the statin acid and/or ammonium salt thereof is heated in a suitable solvent (toluene, butyl acetate, ethyl acetate, cyclohexane) to boiling, whereby the azeotropic mixture of the solvent and water having a lower boiling point distills off first and the reaction equilibrium is thus shifted to the formation of the lactone. The speed of water and, optionally, ammonia removal may be increased by passing a stream of inert gas through the hot reaction mixture. The ambient acidity of the statin acid is believed to be responsible for the lactonization reaction at these high temperatures. This process has been disclosed e.g. in U.S. Pat. Nos. 4,444,784, 4,582,915, 4,820, 850, WO 98-12188 and many others.

An alternate known possibility, described in U.S. Pat. No. 5,393,893, is to perform the lactonization in a two-phase system of an organic solvent, in which the lactone is soluble, and an aqueous acid, whereby the formed water is displaced from the organic layer containing the lactone, to the aqueous layer.

Both alternatives have the disadvantage that elevated temperatures and long reaction times are necessary to be applied for completing the reaction. Statins are sensitive to heating and so the use of such elevated temperatures gives rise to the risk of impurities being formed. One of the most common impurities arises from dimerization of the starting material. For instance, simvastatin of pharmaceutically acceptable quality (e.g. the quality of Ph.Eur. monograph) should contain only less than 0.2% of such dimer.

Another known method is based on the removal of the lactone itself from the reaction medium. In this arrangement, the statin acid or its salt is dissolved in a water-miscible solvent under presence of an acidic catalyst and water is added to the reaction mixture after certain reaction period, as an antisolvent. The lactone is not soluble in water and separates from the solution, thus shifting the equilibrium in the solution to allow formation of the next lactone. This method has been disclosed in EP 351918/U.S. Pat. Nos. 4,916,239 and in 5,159,104. The reaction does not require elevated temperatures so that the potential for forming impurities, particularly dimers, is lower. However, the selection of the water-miscible solvent and the proper amounts and timings of added water is crucial since fast or premature addition of water can lead to serious problems in isolation of the product; i.e., impurities of similar structure present in the starting statin acid may accordingly separate from the solution and decrease the purity of the obtained lactone.

In addition, many of the above lactonization methods of the prior art require relatively long reaction times, typically longer than one hour, for obtaining an acceptable degree of conversion. This, together with the necessary subsequent work-up, makes the prior art methods somewhat complicated to carry out and economically less desirable.

It would be desirable to provide a process for carrying out lactonization that could be done simply in a short amount of time and that ideally would not require a high risk of impurity or dimer formation.

SUMMARY OF THE INVENTION

The present invention is based on the discovery that a lactonization agent can be used that is hydrated by the water produced by the lactonization reaction to form an insoluble hydrated lactonization agent. Because the hydrated complex is insoluble in the reaction medium, the produced water is effectively removed from the reaction and the equilibrium is shifted towards the lactone side. Accordingly, a first aspect of the present invention relates to a process, which comprises subjecting a compound of formula (2):

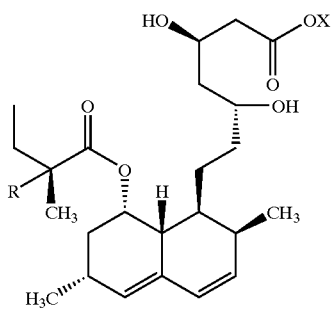

wherein R is a hydrogen atom or a lower alkyl group, and X is a hydrogen atom, a metal cation or an ammonia cation, to a lactonization reaction in a solvent in the presence of a lactonization agent to form a compound of formula (1):

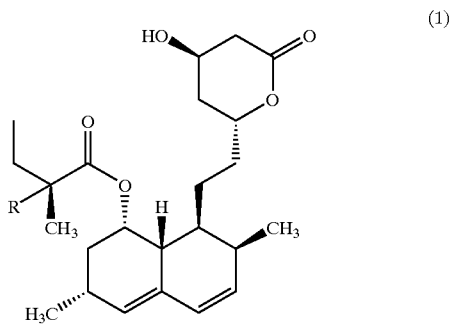

wherein R has the same meaning as above in formula (2) and wherein water released in the lactonization reaction complexes with said lactonization agent to form an insoluble hydrated complex lactonization agent. Preferably R is methyl, which corresponds to simvastatin in formula (1).

Optionally, the process also comprises the steps of removal of the hydrated complex after the reaction from the reaction mixture and isolation of the compound (1) from the reaction medium, preferably without the aid of an antisolvent.

This lactonization of the statin can proceed at ambient temperature (no heating need), is simple and short and is easily operable in industrial scale. Furthermore, the process does not require any special techniques or operations for shifting the equilibrium during the reaction.

DETAILED DESCRIPTION OF THE INVENTION

The starting acid form of simvastatin or lovastatin may be employed in a crude or purified state. A preferred precursor is the ammonium salt of lovastatin or simvastatin acid as this compound may be isolated from reaction mixtures of preceding reaction steps by methods known per se, in a stable crystalline form. Also this salt form may be used in the crude or purified state.

The reaction solvent employed in the process of the invention is generally inert, preferably water immiscible, and one in which the lactone form is sufficiently soluble. The solvent is not a good solvent for the hydrated complex. Preferably the solvent is a good solvent for the acid starting material. However, it is not excluded that the starting compound, e.g. the ammonium salt of the statin acid, may however be only sparingly soluble in the solvent.

In a particularly advantageous embodiment, both the lactonization agent and the chemically converted acidic compound (i.e. the stable hydrated complex) are both essentially insoluble in the solvent and may be thus easily removed from the reaction mixture by filtration after termination of the lactonization reaction.

The solvent employed is preferably anhydrous. Suitable solvents for the process of the invention include hydrocarbons such as benzene, halogenated hydrocarbons especially chlorinated hydrocarbons such as dichloromethane, and acetonitrile.

The lactonization agent is an organic or inorganic lactonization catalyst compound that is generally of an acidic nature, which is able to bind water and, if applicable, the cation or ammonia. The hydrated lactonization agent is referred to frequently as the "hydrated complex." However, it should be understood that the term "complex" is not used in a strict technical sense and embraces any combination of the lactonization produced water and the lactonization agent involving binding, bonding, strong association and/or true complexing. Typically the lactonization agent is in anhydrous form. In some embodiments the lactonization agent is a solid and is thus used as a suspension, slurry, or column packing, in the lactonization reaction solvent.

A preferred lactonization agent is anhydrous methane sulfonic acid. Methane sulfonic acid is able to bind water to form a hydrate and is also able to bind the ammonia if the ammonium salt of a statin is used. The hydrated complex carrying the entrapped water and ammonia is preferably substantially insoluble in the reaction solvent.

Phosphorous pentoxide, an acidic ion-exchange resin, especially a strongly acidic ion-exchange resin such as Dowex 50X2-400, molecular sieves, acid clay or acidic silica gel are the further examples of suitable acidic lactonization agents to bind water and/or ammonia into insoluble compounds. Ion exchange acidic resins are particularly advantageous as they may work in various types of solvents, including polar solvents such as acetonitrile, are easily removable from the reaction mixture after the reaction and may be easily regenerated by conventional procedures. Care is to be taken that the resins are sufficiently dry prior to use.

If the lactonization agent, e.g. ion-exchange resin, molecular sieve, clay or silica gel is not sufficiently acidic by its nature, it may be combined with a desired or necessary amount of an acid directly in the reaction mixture.

The amount of the lactonization agent to be employed may vary depending on the nature of the lactonization agent and the starting material. If ammonium (or another) salt of a statin acid is used, one acid equivalent of the agent is spent to bind the salt cation; the same or next equivalent is necessary to bind water. Preferably, slightly more than the stoichiometric equivalent of the agent is required, as the molar excess of the acidic compound serves for catalysis of the reaction. For instance, a suitable amount of methane sulfonic acid in relation of simvastatin or lovastatin acid ammonium salt is 1–50% molar excess (1.01–1.5 equivalents), while phosphorus pentoxide requires about 50% stoichiometric excess.

The reaction temperature of the process is typically not greater than 50° C. and is preferably within the range of 10° C.–50° C., more preferably 10° C.–40° C., or even 15° C.–35° C. Most preferably the lactonization reaction temperature is essentially ambient temperature, i.e. no heating is added or supplied, and/or is room temperature or about 25° C. The mixture of the starting acid or salt is stirred, preferably under nitrogen atmosphere, together with the lactonization agent without heating or cooling. No control of reaction temperature is generally required.

Progress of the reaction may be monitored by any suitable method allowing separation and determination of the amounts of the starting and formed product in the reaction mixture. Such a suitable method is high performance liquid chromatography (HPLC).

The lactonization process proceeds with a high conversion rate. In some embodiments sufficient conversion, such as more than 90% and preferably more than 95%, may be obtained at ambient temperature in 15–60 minutes. In other embodiments, the lactonization reaction can be carried out for 1 to 3 hours at ambient temperature or even elevated temperatures (30° C.–50° C.) if needed.

For example, after stirring one molar equivalent of ammonium salt of simvastatin acid with 1.3 molar equivalents of anhydrous methane sulfonic acid in dichloromethane at ambient temperature, 85% conversion was observed by HPLC after 5 minutes and 94% conversion was accordingly reached in 15 minutes.

With phosphorus pentoxide, the complete conversion may be reached in 3 hours at ambient temperature.

A strongly acidic ion exchange resin requires the same and sometimes longer reaction times at ambient temperature. For instance, Dowex 50X2-400 resin provided 95% conversion in 2 hours in acetonitrile, while in dichoromethane the reaction required about 24 hours and more for obtaining complete conversion at ambient temperature. A shorter reaction time may be obtained by increasing the reaction temperature, e.g. up to 50° C., whereby the amounts of undesired by-products, particularly the dimer, are still negligible.

As the reaction temperature is mild and reaction time is short, the potential for forming impurities is low. The HPLC confirmed that the dimeric impurity was formed in amounts less than 0.1 mass % under the conditions referred to above. Other types of impurities, for instance products of elimination of the OH-group, are also formed only in negligible amounts.

Insoluble polymeric lactonization agents, e.g. acidic ion-exchange resins may also be employed within the process of our invention in a continual or semicontinual reactor. For instance, the solution of the substrate may be passed or circulated through a column filled with the resin until the sufficient conversion is obtained. The solution comprising the lactonized statin is then elaborated to isolate the statin. This may lead to economic use of the resin and, as well, regeneration of the resin may be simple.

Isolation of a statin from reaction mixture after the lactonisation in a solid state, is also simple and does not require any contrasolvent to precipitate the product, although such is not excluded. In the case of insoluble lactonization agents of the present invention such as ion-exchange resin, its excess (incl. the spent part of such compound that binds water and/or ammonia) is simply removed by filtration. Alternately, the remaining excess of the acidic compound is first neutralized by a proper amount of a base; preferably, organic amines such as triethylamine or pyridine should be employed as such compounds do not react with the acid catalyst under formation of water.

The insoluble neutralized acidic compound is subsequently removed from the reaction mixture by filtration or centrifugation.

Water soluble co-products carrying the bound water or ammonia may alternately be removed from the reaction mixture by extraction with alkalinized water.

The remaining solution comprises the formed lactone. The desired statin may be obtained by crystallization after cooling, optionally after concentration of the solution, or by evaporation of the solution to dryness, yielding the corresponding statin in a solid state.

Crude statin obtained by this process may optionally be subsequently purified to the desired degree of purity by any suitable conventional purification method known per se. For example, it may be crystallized from a proper solvent system or may be chromatographed on a suitable carrier.

Statins produced by the process of the present invention, e.g. simvastatin, may further be used in production of pharmaceutical compositions useful in treatment of various types of hypercholesterolemia. They may be formulated into e.g. tablets or capsules comprising therapeutically effective amount of the active substance together with pharmaceutically acceptable carriers or diluents. The formulation methods may comprise various techniques of blending, filing and/or compressing known in the art.

EXAMPLES

Example 1

Lactonisation of Ammonium Salt of Simvastatin by Methane Sulfonic Acid

A 100 ml three-necked flask equipped with a CaCl2 tube, stirring bar and a nitrogen inlet was charged with 2.5 g of simvastatin ammonium salt, 30 ml of dichloromethane and 690 mg of anhydrous methane sulfonic acid (1.3 molar equivalent). The resulting suspension was stirred at room temperature under a nitrogen atmosphere for 15 minutes. Then, 170 mg of triethylamine was added and after 10 minutes of stirring the solid was filtered off. The clear solution was evaporated to dryness. The rest after evaporation was dissolved in 21 ml of ethanol/water (1:1 v/v) mixture under elevated temperature and crystallized by subsequent leaving overnight at room temperature. The precipitated solid was filtered off and washed with a small amount of the same ethanol/water mixture. Yield of simvastatin after drying: 1.8 g (80%).

The crude product (1 g) was recrystallized to obtain 0.82 g of pure simvastatin with dimer content 0.1 mass % (HPLC).

Example 2

Lactonisation of Ammonium Salt of Simvastatin by Phosphorus Pentoxide

A 100 ml flask equipped with CaCl2 tube, stirring bar and nitrogen inlet was charged with 2.5 g of simvastatin ammonium salt and 30 ml of dichloromethane. To the stirred mixture, 1.17 g of phosphorus pentoxide was added in one portion. The resulting suspension was stirred at room temperature under nitrogen. After complete conversion (HPLC), the reaction mixture was treated with 5% solution of $NaHCO_3$ and extracted with 3×100 ml of ethyl acetate. The organic layer was washed with water, dried by magnesium sulfate and the solvent was removed in vacuo to yield 1.67 g of simvastatin. The product was recrystallized in 62% yield and dimer content 0.08% (HPLC).

Example 3

Lactonization of Ammonium Salt of Simvastatin by Ion-Exchange Resin

A)

Dowex 50X2-400 resin was washed with water, methanol and ether and dried at 70° C. 2.5 g of simvastatin ammonium salt was suspended in 50 ml of dichloromethane under nitrogen and 2.5 g of the pre-dried Dowex resin was added. The mixture was stirred at room temperature. After two days the resin was removed by filtration and washed with dichloromethane. The combined filtrates were evaporated at reduced pressure to obtain 2.31 g of a white solid. The product was recrystallized in 82% yield. Dimer content 0.06%.

B)

The above experiment was repeated using acetonitrile as a solvent. After 2 hours, the HPLC analysis of the reaction mixture shows 95% conversion. The reaction was terminated after 6 hours and elaborated as above to obtain simvastatin as white crystals in 95% yield and of 99% purity by UPLC (dimer content 0.05%). After recrystallization from ethanol/water, the purity increased to 99.5%.

C)

The above experiment B) was repeated, but the reaction temperature was increased to 50° C. The reaction was terminated after 4 hours and elaborated as above to obtain simvastatin as a sticky solid mass. After crystallization, simvastatin with 99.3% purity (HPLC) was obtained.

Example 4

Lactonization of Simvastatin Acid by Phosphorus Pentoxide

A 100 ml flask equipped with CaCl2 tube, stirring bar and nitrogen inlet was charged with 2.4 g of simvastatin acid and 30 ml of dichloromethane. To the stirred mixture, 1.17 g of phosphorus pentoxide was added in one portion. The resulting suspension was stirred at room temperature under nitrogen. After complete conversion (HPLC), the reaction mixture was treated with 5% solution of $NaHCO_3$ and extracted with 3×100 ml of ethyl acetate. The organic layer was washed with water, dried by magnesium sulfate and the solvent was removed in vacuo. The rest was dissolved in 12 ml of toluene, 40.5 ml of cyclohexane was added and the mixture was heated until a clear solution was obtained. The solution was stored overnight at room temperature, the precipitated crystals were filtered off, washed with cyclohexane, and dried to give 1.95 g of simvastatin.

The present application claims the benefit of priority under 35 U.S.C. §119 from the prior The Netherlands patent application serial No. 1017548, filed Mar. 9, 2001, the entire contents of which are incorporated herein by reference.

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A process which comprises subjecting a compound of formula (2):

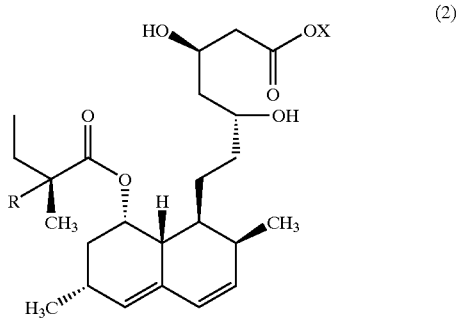

wherein R is a hydrogen atom or a lower alkyl group, and X is a hydrogen atom, a metal cation or an ammonia cation, to a lactonization reaction in a solvent in the presence of a lactonization agent to form a compound of formula (1):

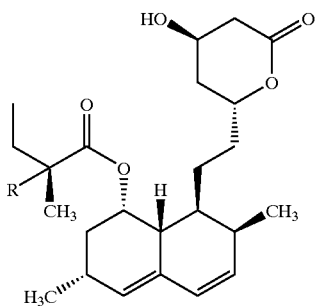

(1)

wherein R has the same meaning as above in formula (2) and wherein water released in the lactonization reaction complexes with said lactonization agent to form an insoluble hydrated complex lactonization agent.

2. The process according to claim 1, wherein said compound of formula (1) is dissolved in said solvent and which further comprises removing said hydrated complex from said solvent.

3. The process according to claim 2, wherein said lactonization agent is insoluble in said solvent.

4. The process according to claim 2, wherein said hydrated complex is removed by filtration.

5. The process according to claim 2, wherein said hydrated complex is removed by means of extraction with alkalinized water.

6. The process according to claim 1, wherein the solvent is substantially immiscible with water.

7. The process according to claim 1, wherein said solvent is a hydrocarbon, a halogenated hydrocarbon, mixtures thereof, or acetonitrile.

8. The process according to claim 7, wherein said solvent is dichloromethane or acetonitrile.

9. The process according to claim 1, wherein the lactonization agent is substantially anhydrous.

10. The process according to claim 1, wherein the lactonization agent is selected from the group consisting of methane sulfonic acid, phosphorus pentoxide, acidic ion-exchange resin, molecular sieves, acid clay, acidic silica gel, and combinations thereof.

11. The process according to claim 10, wherein the lactonization agent is anhydrous methane sulfonic acid and/or an acidic ion-exchange resin.

12. The process according to claim 1, wherein said lactonization agent binds ammonia upon forming the hydrated complex.

13. The process according to claim 1, wherein the molar ratio between compound (2) and the lactonization agent is roughly 1:1.01 to 1:1.5.

14. The process according to claim 1, wherein said lactonization reaction proceeds at a temperature not exceeding 50° C.

15. The process according to claim 14, wherein said lactonization reaction proceeds without heating the reaction.

16. The process according to claim 1, wherein said lactonization reaction is carried out for 15 to 60 minutes.

17. The process according to claim 1, which further comprises isolating compound (1) from said solvent.

18. The process according to claim 17, wherein said compound of formula (1) is simvastatin.

19. The process according to claim 18, wherein said compound of formula (2) is the ammonium salt of simvastatin acid.

20. The process according to claim 1, wherein said lactonization agent is an anhydrous organic or inorganic lactonization catalyst and said solvent is acetonitrile.

* * * * *